(12) United States Patent
Allum

(10) Patent No.: US 11,964,105 B2
(45) Date of Patent: Apr. 23, 2024

(54) OXYGEN GAS CONCENTRATOR WITH OUTLET ACCUMULATOR

(71) Applicant: INOGEN, INC., Goleta, CA (US)

(72) Inventor: Todd Allum, Livermore, CA (US)

(73) Assignee: INOGEN, INC., Goleta, CA (US)

( * ) Notice: Subject to any disclaimer, the term of this patent is extended or adjusted under 35 U.S.C. 154(b) by 600 days.

(21) Appl. No.: 17/063,708

(22) Filed: Oct. 5, 2020

(65) Prior Publication Data

US 2021/0016044 A1  Jan. 21, 2021

Related U.S. Application Data

(63) Continuation of application No. 15/706,616, filed on Sep. 15, 2017, now Pat. No. 10,792,453, which is a
(Continued)

(51) Int. Cl.
*B01D 53/02* (2006.01)
*A61M 16/06* (2006.01)
(Continued)

(52) U.S. Cl.
CPC ...... *A61M 16/101* (2014.02); *A61M 16/0672* (2014.02); *A61M 16/106* (2014.02);
(Continued)

(58) Field of Classification Search
CPC .............. A61K 31/5415; A61M 16/00; A61M 16/0057; A61M 16/0672; A61M 16/101; A61M 16/106; A61M 16/107; A61M 16/201; A61M 16/208; A61M 2016/0027; A61M 2016/003; A61M 2016/1025; A61M 2205/3331; A61M 2205/3334; A61M 2205/50; A61M 39/24; B01D 2221/10; B01D 2253/108; B01D 2256/12; B01D 2257/102; B01D 2258/06; B01D 2259/402; B01D 2259/4533; B01D 2259/4541; B01D 53/053; C01B 13/0259; C12Q 1/6886; C12Q 2600/106; C12Q 2600/118; C12Q 2600/158; G16B 20/00; G16B 25/10; G16B 40/10; G16B 40/20
See application file for complete search history.

(56) References Cited

U.S. PATENT DOCUMENTS 4,983,190 A   1/1991 Verrando et al.
5,578,115 A   11/1996 Cole
(Continued)

OTHER PUBLICATIONS

Oxygen Gas Concentrator With Outlet Accumulator, U.S. Appl. No. 15/706,616, U.S. Pat. No. 10,792,453.
(Continued)

*Primary Examiner* — Christopher P Jones
(74) *Attorney, Agent, or Firm* — Knobbe, Martens, Olson & Bear, LLP

(57) ABSTRACT

An oxygen concentrator comprises a product tank that is fluidly coupled to at least one sieve bed, and a product gas accumulator tank that is fluidly coupled to the product tank via a first conduit and to an outlet port via a second conduit, wherein the first conduit and the second conduit are disposed to allow at least a portion of product gas to flow from the product tank to the outlet port.

14 Claims, 7 Drawing Sheets

Related U.S. Application Data continuation of application No. 15/603,380, filed on May 23, 2017, now abandoned.

(60) Provisional application No. 62/341,021, filed on May 24, 2016.

(51) Int. Cl.
| | |
|---|---|
| *A61M 16/10* | (2006.01) |
| *A61M 39/24* | (2006.01) |
| *B01D 53/053* | (2006.01) |
| *C01B 13/02* | (2006.01) |
| *A61M 16/00* | (2006.01) |
| *A61M 16/20* | (2006.01) |

(52) U.S. Cl.
CPC ........... *A61M 39/24* (2013.01); *B01D 53/053* (2013.01); *C01B 13/0259* (2013.01); *A61M 16/00* (2013.01); *A61M 2016/0027* (2013.01); *A61M 2016/003* (2013.01); *A61M 16/0057* (2013.01); *A61M 2016/1025* (2013.01); *A61M 16/107* (2014.02); *A61M 16/201* (2014.02); *A61M 16/208* (2013.01); *A61M 2205/3331* (2013.01); *A61M 2205/3334* (2013.01); *A61M 2205/50* (2013.01); *B01D 2221/10* (2013.01); *B01D 2253/108* (2013.01); *B01D 2256/12* (2013.01); *B01D 2257/102* (2013.01); *B01D 2258/06* (2013.01); *B01D 2259/402* (2013.01); *B01D 2259/4533* (2013.01); *B01D 2259/4541* (2013.01)

(56) References Cited

U.S. PATENT DOCUMENTS

| | | | |
|---|---|---|---|
| 5,720,276 | A | 2/1998 | Kobatake et al. |
| 6,302,107 | B1 * | 10/2001 | Richey ............ A61M 16/101 |
| | | | 95/96 |
| 2002/0038656 | A1 | 4/2002 | Yagi et al. |
| 2002/0053286 | A1 | 5/2002 | Czabala |
| 2004/0079359 | A1 | 4/2004 | Aylsworth et al. |
| 2006/0174881 | A1 | 8/2006 | Jagger et al. |
| 2008/0135044 | A1 | 6/2008 | Freitag et al. |
| 2008/0178881 | A1 | 7/2008 | Whitcher et al. |
| 2009/0293879 | A1 | 12/2009 | Fraanberg |
| 2012/0272966 | A1 | 11/2012 | Ando et al. |
| 2013/0025591 | A1 | 1/2013 | Clark et al. |
| 2013/0205997 | A1 | 8/2013 | Sommier et al. |
| 2014/0137744 | A1 | 5/2014 | Wilkinson et al. |
| 2015/0107585 | A1 | 4/2015 | Allum |
| 2015/0196727 | A1 | 7/2015 | Ahmad |
| 2016/0279362 | A1 | 9/2016 | Devries et al. |
| 2016/0310886 | A1 * | 10/2016 | Von Hollen ........ A61M 16/101 |
| 2019/0134340 | A1 | 5/2019 | Nebrigac |

OTHER PUBLICATIONS

Oxygen Gas Concentrator With Outlet Accumulator, U.S. Appl. No. 15/603,380, 2017/0340851 A1.

International Search Report and Written Opinion for PCT Application No. PCT/US2017/034332 dated Sep. 21, 2017, 20 pages.

* cited by examiner

OXYGEN GAS CONCENTRATOR WITH OUTLET ACCUMULATOR

CROSS-REFERENCE TO RELATED APPLICATIONS

This application is a continuation of co-pending U.S. patent application titled "OXYGEN GAS CONCENTRATOR WITH OUTLET ACCUMULATOR," filed on Sep. 15, 2017 and having Ser. No. 15/706,616, which is a continuation of U.S. patent application titled, "OXYGEN GAS CONCENTRATOR WITH OUTLET ACCUMULATOR," filed on May 23, 2017 and having Ser. No. 15/603,380, which claims priority benefit of the United States Provisional patent application titled, "Addition of an Outlet Accumulator to a High Pressure Concentrator to allow Use of either a Ventilator or Nasal Cannula," filed on May 24, 2016 and having Ser. No. 62/341,021. The subject matter of these related applications is hereby incorporated herein by reference.

BACKGROUND OF THE INVENTION

Field of the Invention

The present invention relates generally to medical devices and, more specifically, to an oxygen gas concentrator with an outlet accumulator.

Description of the Related Art

Oxygen therapy is the standard of care for many patients with lung diseases in the early to mid-stages. In particular, individuals with Chronic Obstructive Pulmonary Disease (COPD), the third leading cause of death in the United States, are prescribed with oxygen therapy to increase blood oxygen saturation. In many cases, patients with COPD can also benefit from improved ventilation of the lungs to help evacuate elevated levels of carbon dioxide. However, because of the high cost and large sizes of traditional mechanical ventilators, such patients are generally not prescribed ventilation therapy until hospitalized or in the late stages of the disease even though ventilation therapy, and ventilation with oxygen therapy have all proven to be beneficial therapies for patients with COPD (with increasing benefit, respectfully). Consequently, the use of oxygen concentrators in conjunction with mechanical ventilators has been studied as a means to reduce the cost of ventilation with oxygen therapy.

However, oxygen concentrators are generally not well-suited for direct coupling with mechanical ventilators. Specifically, ventilators generally require a gas source that can provide a spontaneous flow rate of more than 100 liters per minute (LPM) to provide adequate ventilation therapy during an inspiratory effort, while a typical oxygen concentrator can deliver a continuous flow rate on the order of only about 1 to 10 LPM. Accordingly, a conventional oxygen concentrator is generally incapable of meeting the large spontaneous flow rate requirements of a typical ventilator that is being used to assist the inspiratory efforts of a patient. Among other things, depletion of the product tank in the oxygen concentrator can occur. Product tank depletion, in which the product gas pressure in the product tank falls below a target minimum target pressure, reduces the expected flow rate of product gas delivered to the ventilator, which is highly undesirable.

To prevent product tank depletion when an oxygen concentrator is used in conjunction with a ventilator, the operating pressure of the product tank can be elevated. With the higher product tank pressure, more product gas is available for each inspiratory effort of the patient. However, higher product tank pressure puts significantly greater demand on the oxygen concentrator compressor, resulting in more heat dissipation and noise, increased energy expenditure, and reduced compressor life.

Alternatively, the product tank of the oxygen concentrator can be increased in size such that more product gas is available for each inspiratory effort of the patient. However, a larger product tank generally results in an oxygen concentrator that is heavier and more expensive than a conventional oxygen concentrator. Furthermore, while the increased size of the product tank theoretically makes more product gas available for each inspiratory effort of the patient, in practice the pressure drop in the system between the product tank and the concentrator outlet prevents the added capacity of the product tank from maintaining a constant outlet pressure throughout a patient's inspiratory efforts.

As the foregoing illustrates, what is needed in the art are more effective ways to interface oxygen concentrators with mechanical ventilators.

SUMMARY OF THE INVENTION

One embodiment of the present invention sets forth an oxygen concentrator that is configured for use in conjunction with a mechanical ventilator. The oxygen concentrator includes a product tank that is fluidly coupled to at least one sieve bed, and a product gas accumulator tank that is fluidly coupled to the product tank via a first conduit and to an outlet port via a second conduit, wherein the first conduit and the second conduit are disposed to allow at least a portion of product gas to flow from the product tank to the outlet port passes through the accumulator tank.

At least one advantage of the disclosed design is that an oxygen concentrator can be connected to a mechanical ventilator and provide a more constant flow of product gas to the mechanical ventilator relative to prior art designs.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1A:
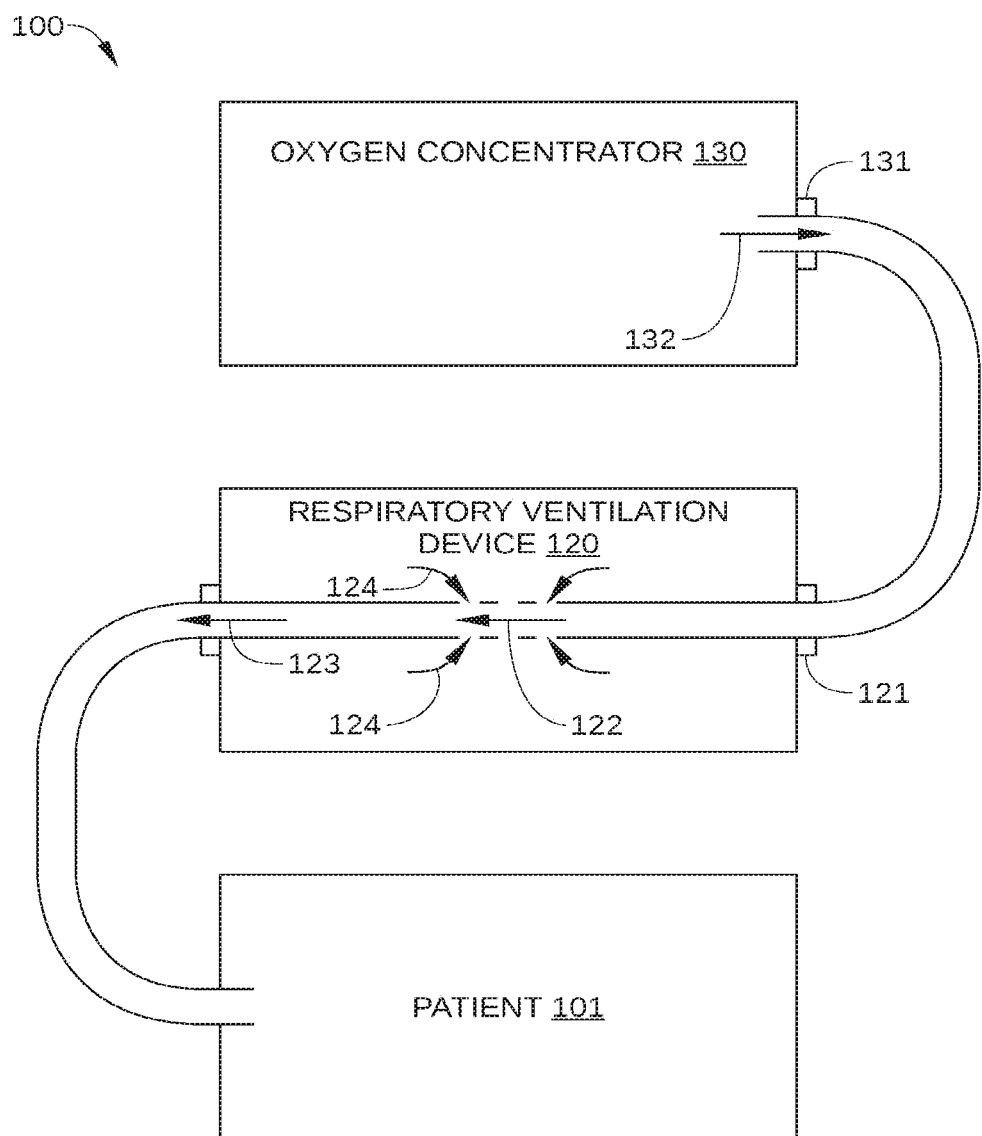
FIG. 1A is a block diagram of an oxygen-ventilation therapy system, according to various embodiments of the present invention.

In the following description, numerous specific details are set forth to provide a more thorough understanding of the embodiments of the present invention. However, it will be apparent to one of skill in the art that the embodiments of the present invention may be practiced without one or more of these specific details.

Stationary and portable oxygen concentrators commonly employ a process called pressure swing adsorption (PSA) to increase the oxygen concentration of the incoming ambient air before the air is delivered to a patient. Generally, the delivered oxygen concentration is between 90 and 96%, due to concentrator efficiencies and remaining constituent elements in the air that are not adsorbed in the process. Stationary and most portable oxygen concentrators use the PSA process to deliver a constant flow of oxygen to the patient, typically 1 to 5 LPM, and in some cases up to 10 LPM As noted above, the continuous flow rate of oxygen concentrators is generally too low to serve as a sole gas source for conventional mechanical ventilators: typical ventilators require a source of supply gas that can provide a flow rate of about 100 LPM to provide adequate ventilation therapy during an inhalation. However, ventilators that utilize entrainment technology only require approximately 20 LPM of flow from the ventilator gas source during an inhalation to provide 100 LPM of ventilation support. For a spontaneous intermittent ventilator, the average delivered volume from the gas source (minute volume) is based on the flow during inhalation, the inhalation delivery period and the patient's breath rate. The source gas minute volume requirements of a ventilator that utilizes entrainment technology typically ranges from 1 to 5 LPM, which is well within the continuous flow rate provided by most stationary oxygen concentrators.

According to embodiments of the invention, the output of an oxygen concentrator, i.e., oxygen-enriched product gas, is fluidly connected to a respiratory ventilation device, thereby facilitating oxygen and ventilation therapy. Furthermore, to meet and maintain a targeted operating oxygen flow for the respiratory ventilation device, the oxygen concentrator includes an accumulator tank that is disposed at or near an outlet port of the oxygen concentrator. The accumulator tank is configured to prevent product tank depletion in the oxygen concentrator during the high product gas demand from the respiratory ventilation device that occurs during each patient inspiratory effort, thereby ensuring that product gas is supplied to the respiratory ventilation device at a consistent flow rate. Specifically, the accumulator tank is configured to temporarily store product gas between each patient inspiratory effort and to supply the stored product gas at a consistent flow rate during each patient inspiratory effort. As a result, pressure swings in the product tank of the oxygen concentrator are reduced in response to product gas demand from the respiratory ventilation device, and product tank depletion is prevented.

FIG. 1A is a block diagram of an oxygen-ventilation therapy system 100, according to various embodiments of the present invention. Oxygen-ventilation therapy system 100 is configured to simultaneously provide both oxygen therapy and ventilation therapy to a patient 101, and includes a respiratory ventilation device 120 and an oxygen concentrator 130. As shown, an output 131 of oxygen concentrator 130 is fluidly coupled to an inlet 121 of respiratory ventilation device 120, so that respiratory ventilation device 120 provides oxygen-enriched inhalation gas 123 to patient 101 during ventilation therapy.

Respiratory ventilation device 120 may be any technically feasible respiratory ventilator capable of moving breathable air into the lungs of patient 101. Thus, respiratory ventilation device 120 facilitates the breathing of patient 101, who may be physically unable to breathe, or may be breathing insufficiently. Inhalation gas 123 may be delivered from respiratory ventilation device 120 to patient 101 by a nasal mask, nasal cannula, intubation, or the like.

In some embodiments, respiratory ventilation device 120 is configured to employ entrainment of ambient air in the delivery of inhalation gas 123 to patient 101. In such embodiments, respiratory ventilation device 120 directly provides a source gas 122 that is only a portion of the inhalation gas 123 inhaled by patient 101. The remaining portion of inhalation gas 123 is ambient air 124, which has been entrained by source gas 122. In general, source gas 122 is typically a relatively small portion of inhalation gas 123, for example between about 10% to 50% of inhalation gas 123. Thus, when the instantaneous flow rate requirement for respiratory ventilation device 120 during an inhalation by patient 101 is, for example, 100 LPM, the instantaneous flow rate requirement for inhalation gas 123 is also 100 LPM, while the instantaneous flow rate requirement for source gas 122 is only about 10 to 30 LPM. In such embodiments, most or all of source gas 122 may be provided by oxygen concentrator 130 as an oxygen-enriched product gas 132. Alternatively, source gas 122 may include a combination of an oxygen-enriched product gas 132 and ambient air that is mixed with oxygen-enriched product gas 132.

Oxygen concentrator 130 is configured to produce oxygen-enriched product gas 132 for providing oxygen therapy to patient 101. Thus, patient 101 receives both ventilation therapy via respiratory ventilation device 120 and oxygen therapy. According to various embodiments, oxygen concentrator 130 may employ any technically feasible oxygen concentration process for providing oxygen-enriched product gas 132. For example, oxygen concentrator 130 may be configured to employ a pressure swing adsorption (PSA) process, a rapid pressure swing adsorption (RPSA) process, a vacuum pressure swing adsorption (VPSA), or any other derivative process thereof. In each case, oxygen concentrator 130 is configured to provide a targeted flow rate of product gas 132 for each inspiratory effort of patient 101. To that end, 130 is configured with an accumulator tank, as described below in conjunction with FIG. 2.

In some embodiments, oxygen concentrator 130 is configured as a conventional semi-portable (wheeled) or non-portable (stationary) oxygen concentrator, for example for use in a home or hospital setting. In other embodiments, oxygen concentrator 130 is a portable oxygen concentrator, such as a device configured to be carried in a backpack. In such embodiments, respiratory ventilation device 120 may also be configured as a portable or ultra-portable device.

Figure 1B:
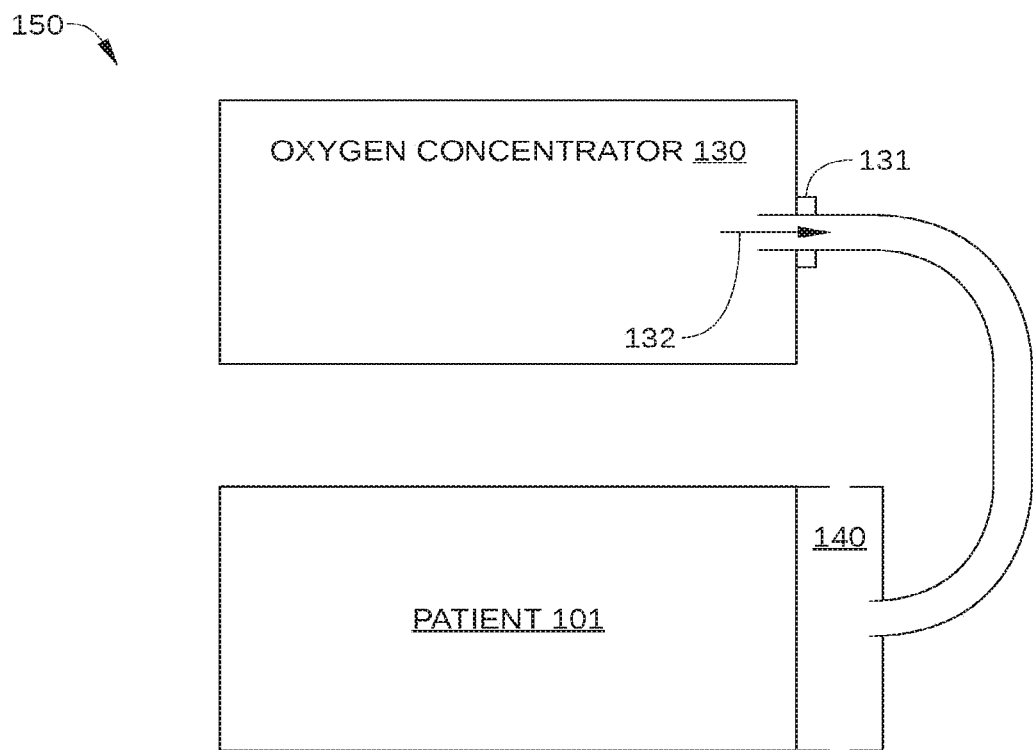
FIG. 1B is a block diagram of an oxygen therapy system, according to various other embodiments of the present invention.

FIG. 1B is a block diagram of an oxygen therapy system 150, according to various other embodiments of the present invention. Oxygen therapy system 150 is configured to provide oxygen therapy to a patient 101 without ventilation therapy, and includes oxygen concentrator 130. As shown, output 131 of oxygen concentrator 130 is fluidly coupled to an ambient pressure delivery device 140, such as a nasal cannula, a nasal mask, or any other device configured to deliver supplemental oxygen to patient 101 at ambient pressure. During operation oxygen therapy system 150 supplies oxygen-enriched product gas 132 directly to patient 101 via a continuous flow of oxygen-enriched product gas 132 via ambient pressure delivery device 140.

Figure 2:
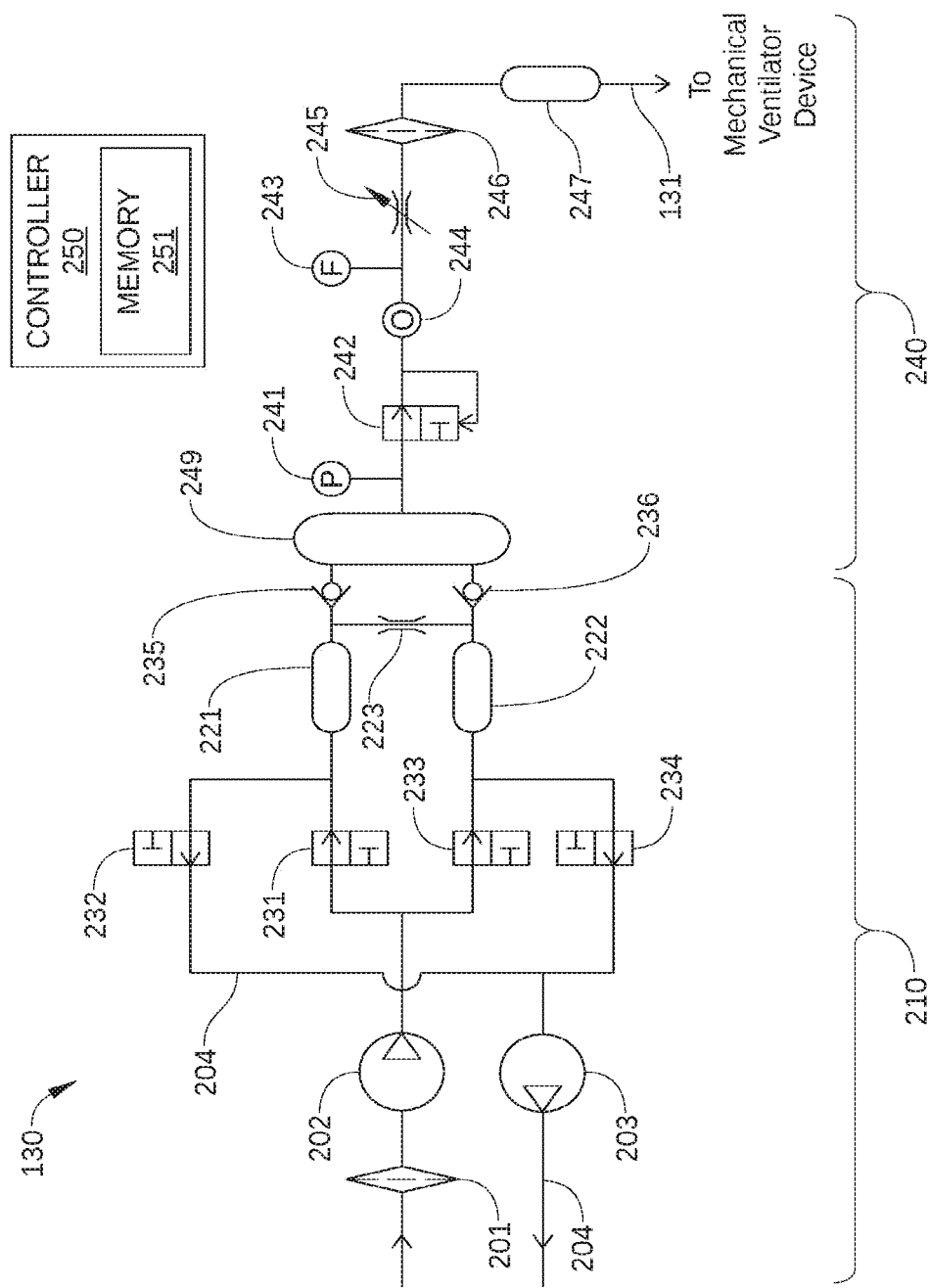
FIG. 2 is a more detailed schematic illustration of the oxygen concentrator of FIGS. 1A and 1B, according to various embodiments of the present invention.

FIG. 2 is a more detailed schematic illustration of oxygen concentrator 130, according to various embodiments of the present invention. As noted above, oxygen concentrator 130 is configured to produce an oxygen-enriched product gas to a patient who is receiving oxygen-ventilation therapy via oxygen-ventilation therapy system 100 or who is receiving oxygen therapy via oxygen therapy system 150. As such, oxygen concentrator 130 includes, without limitation, a product gas generation stage 210, a product gas supply stage 240, and a controller 250. Product gas generation state 210 is configured to generate a product gas, such as oxygen-enriched product gas 132, and product gas supply stage 240 is configured to store and supply the product gas to patient 101, either via respiratory ventilation device 120 or ambient pressure delivery device 140.

In the embodiment of oxygen concentrator 130 illustrated in FIG. 2, product gas generation stage 210 includes, without limitation, an inlet filter 201, a pump 202, and, in some embodiments, a vacuum pump 203, all connected via pneumatic plumbing 204, as shown in FIG. 2. Product gas generation stage 210 further includes, without limitation, a first sieve bed 221 and a second sieve bed 222, fluidly connected to each other by an equalization orifice 223. First sieve bed 221 and second sieve bed 222 are each configured to remove nitrogen from air present therein, so that product gas exiting first sieve bed 221 or second sieve bed 222 is an oxygen-enriched gas. Typically, first sieve bed 221 and second sieve bed 222 each include a nitrogen-adsorbing material, such as a nitrogen-adsorbing zeolite. Consequently, as air flows into one of first sieve bed 221 or second sieve bed 222, the air passes through the nitrogen-adsorbing material, a significant portion of the nitrogen is adsorbed, and the remaining gas in the sieve bed is primarily oxygen. This oxygen-enriched gas can then flow into a product tank 249.

Product gas generation stage 210 further includes, without limitation, a first sieve bed fill valve 231 coupled to an inlet of first sieve bed 221, a first sieve bed dump valve 232 fluidly coupled to an outlet of first sieve bed 221, a second sieve bed fill valve 233 coupled to an inlet of second sieve bed 222, and a second sieve bed dump valve 234 fluidly coupled to an outlet of second sieve bed 222. First sieve bed fill valve 231 is a controllable valve that selectively allows entry of air or any other suitable gas to enter first sieve bed 221. First sieve bed dump valve 232 is a controllable valve that selectively allows gas present in first sieve bed 221 to exit first sieve bed 221 when at a higher pressure than ambient. Second sieve bed fill valve 233 and second sieve bed dump valve 234 operate similarly with respect to second sieve bed 222.

In the embodiment of oxygen concentrator 130 illustrated in FIG. 2, product gas supply stage 240 generally includes, without limitation, product tank 249, which is fluidly connected to first sieve bed 221 and second sieve bed 222, a first check valve 235, and a second check valve 236. First check valve 235 is disposed between first sieve bed 221 and product tank 249 and is configured to prevent flow or pressure from exiting product tank 249 and entering first sieve bed 221. Similarly, second check valve 236 is disposed between second sieve bed 222 and product tank 249 and is configured to prevent flow or pressure from exiting product tank 249 and entering second sieve bed 222.

In some embodiments, product gas supply stage 240 may further include one or more of a tank pressure measurement device 241, a pressure regulator 242, a flow measurement device 243, an oxygen sensor 244, a manual flow-control device 245, such as an adjustable orifice, an outlet filter 246, and an accumulator tank 247, each disposed downstream of product tank 249 as shown, or in any other configuration that is suitable for operation of oxygen concentrator 130 as described herein. Tank pressure measurement device 241 measures the current pressure in product tank 249 and transmits the measured pressure to controller 210. Pressure regulator 242 is disposed downstream of product tank 249, and is configured to regulate the higher product tank pressure down to a target delivery pressure in a downstream portion of product gas supply stage 240. Thus, oxygen-enriched product gas 132 that is at the current product tank pressure flows from a first conduit or other portion of product gas supply stage 240, through pressure regulator 242, to enter a second conduit or other portion of product gas supply stage 240 at the target delivery pressure. For example, one such target delivery pressure may be a maximum inlet pressure that is recommended for proper operation of respiratory ventilation device 120. Flow measurement device 243 measures flow of oxygen-enriched product gas 132 and transmits the measured flow to controller 210, and oxygen sensor 244 measures the current oxygen concentration of oxygen-enriched product gas 132 and transmits the measured oxygen concentration to controller 210. Manual flow-control device 245 controls the continuous flow rate of oxygen-enriched product gas 132 when oxygen concentrator 130 is coupled to ambient pressure delivery device 140. In some embodiments, manual flow-control device 245 includes an adjustable orifice, such as a rotameter coupled to a needle valve. Outlet filter 246 removes particulates from oxygen-enriched product gas 132 before delivery to patient 101.

Accumulator tank 247 is a storage vessel configured to store some quantity of oxygen-enriched product gas 132 during operation of oxygen concentrator 130. As set forth above, when output 131 of oxygen concentrator 130 is fluidly coupled to respiratory ventilation device 120, accumulator tank 247 is configured to temporarily store oxygen-enriched product gas 132 between each patient inspiratory effort and to supply the stored product gas at a consistent flow rate during each patient inspiratory effort. Consequently, product tank depletion in oxygen concentrator 130 can be prevented during the high product gas demand that can occur during each patient inspiratory effort, thereby ensuring that product gas is supplied to respiratory ventilation device 120 at a consistent flow rate. Prevention of product tank depletion is described in greater detail below in conjunction with FIG. 5. By contrast, when output 131 of oxygen concentrator 130 is fluidly coupled to ambient pressure delivery device 140, pressure in accumulator tank 247 generally decays to approximately ambient pressure plus whatever pressure drop is associated with the flow of oxygen-enriched product gas 132 to and through ambient pressure delivery device 140.

In some embodiments, accumulator tank 247 is configured as a constant volume pressure vessel that stores oxygen-enriched product gas 132, such as a metallic cylinder and the like. In such embodiments, volume demand from respiratory ventilation device 120 results in pressure drop in accumulator tank 247 as oxygen-enriched product gas 132 exits accumulator tank 247 to satisfy the volume demand. In some embodiments, accumulator tank 247 is configured as a constant pressure/variable volume storage vessel that maintains a constant or substantially constant pressure therein even as oxygen-enriched product gas 132 exits accumulator tank 247. In one such embodiment, accumulator tank 247 is configured as a balloon accumulator that includes an elastic membrane or is formed from an elastic material. In another such embodiment, accumulator tank 247 is configured as a constant pressure cylinder or other pressure vessel with a movable piston that is driven by a spring or pneumatic pressure to exert a substantially constant pressure on gas stored therein. The constant pressure cylinder can maintain substantially constant pressure on gas stored therein across a wide range of volumes, thereby providing a constant supply pressure to respiratory ventilation device 120.

Controller 250 is coupled to one or more of first sieve bed fill valve 231, first sieve bed dump valve 232, second sieve bed fill valve 233, second sieve bed dump valve 234, and any sensors included in oxygen concentrator 130. Controller 250 may be any suitable processor implemented as a central processing unit (CPU), an application-specific integrated circuit (ASIC), a field programmable gate array (FPGA), any other type of processing unit, or a combination of different processing units. In general, controller 250 may be any technically feasible hardware unit capable of processing input signals or other data and/or executing software applications to facilitate operation of oxygen concentrator 130 as described herein. Furthermore, in some embodiments, controller 250 may include a memory 251. Memory 251 may include volatile memory, such as a random access memory (RAM) module, and non-volatile memory, such as a flash memory unit, a read-only memory (ROM), or any other type of memory unit or combination thereof suitable for use in controller 250. In such embodiments, memory 251 is configured to store any instructions, software programs, operating system, drivers, and the like, that facilitate operation of controller 250 and any processors making up controller 250.

In operation, oxygen concentrator 130 generates oxygen-enriched product gas 132 via a process that includes a fill phase for each of first sieve bed 221 and second sieve bed 222, a dump phase for each of first sieve bed 221 and second sieve bed 222, and an equalization phase. The fill phase for first sieve bed 221 occurs concurrently with the dump phase for second sieve bed 222, while the fill phase for second sieve bed 222 occurs concurrently with the dump phase for first sieve bed 221. By contrast, the equalization phase for first sieve bed 221 and the equalization phase for second sieve bed 221 occur simultaneously.

Figure 3:
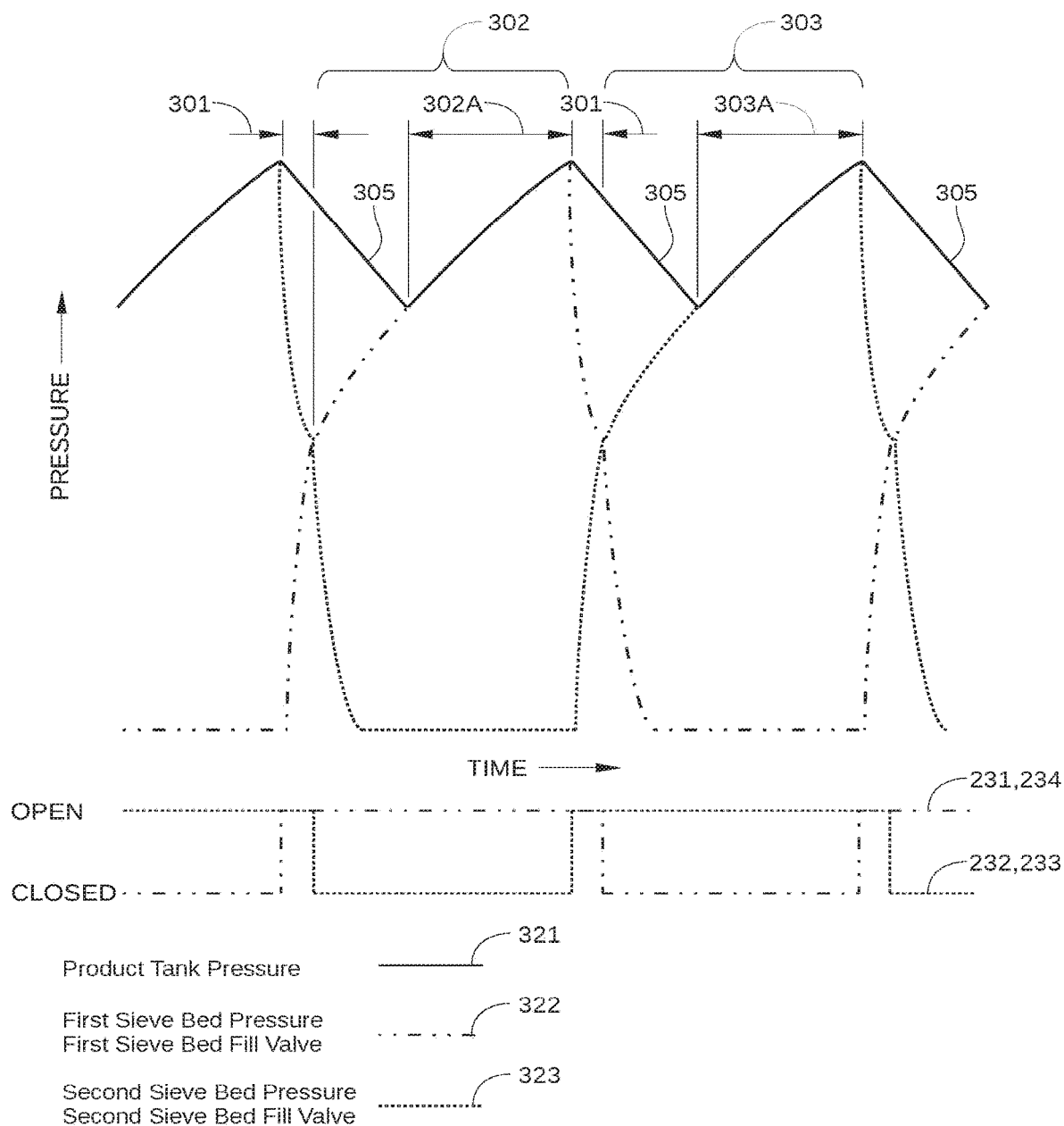
FIG. 3 is a graph illustrating pressure at various locations within a conventional oxygen concentrator of FIG. 1B when the oxygen concentrator is fluidly coupled to the ambient pressure delivery device of FIG. 1B, according to various embodiments of the invention.

FIG. 3 is a graph illustrating pressure at various locations within a conventional oxygen concentrator while the oxygen concentrator is fluidly coupled to ambient pressure delivery device 140 and provides a constant flow of oxygen-enriched gas, according to various embodiments of the invention. Thus, the conventional oxygen concentrator delivers a constant flow of an oxygen-enriched gas 132, for example to patient 101 in FIG. 1. The conventional oxygen concentrator may be substantially similar to oxygen concentrator 130, except without accumulator tank 247. The process by which the conventional oxygen concentrator provides the oxygen-enriched gas includes an equalization phase 301, a first dump/fill phase 302, and a second dump/fill phase 303. A product tank pressure 321, a first sieve bed pressure 322, and a second sieve bed pressure 323 are all depicted over the course of equalization phase 301, first dump/fill phase 302, and second dump/fill phase 303. In addition, the actuations of first sieve bed fill valve 231 and second sieve bed fill valve 233 are shown. Also depicted in FIG. 3 are a first fill time 302A, in which product tank 249 is filled from first sieve bed 221, and a second fill time 303A, in which product tank 249 is filled from second sieve bed 222. It is noted that the filling phase for first sieve bed 221 and the dump phase for second sieve bed 222 take place during first dump/fill phase 302, while the fill phase for second sieve bed 222 and the dump phase for first sieve bed 221 take place during second dump/fill phase 303.

In the filling phase for first sieve bed 221 (i.e., first dump/fill phase 302), the output of pump 202, which is controlled by first sieve bed fill valve 231 and second sieve bed fill valve 233, is directed to first sieve bed 221, in which nitrogen is removed and an oxygen-enriched gas is formed. As a result, the pressure in first sieve bed 221 increases as shown. When pressure in first sieve bed 221 increases to a level equal to the pressure in product tank 249, first fill time 302A begins. That is, first sieve bed pressure 322 is equal to product tank pressure 321, the corresponding check valve (i.e., first check valve 235) opens, the oxygen-enriched gas in first sieve bed 221 enters product tank 249, and the pressure in product tank 249 increases in parallel with and equal to the pressure in first sieve bed 221, as shown.

The dump phase for second sieve bed 222 also occurs during first dump/fill phase 302 (and concurrent with the above-described filling phase for first sieve bed 221). In the dump phase for second sieve bed 222, second sieve bed dump valve 234 is open to ambient, so that accumulated nitrogen within second sieve bed 222 is dumped and the pressure in second sieve bed decreases as shown.

It is noted that, as pump 202 fills first sieve bed 221 and the pressure therein exceeds the pressure in second sieve bed 222, a portion of the oxygen-enriched gas formed in first sieve bed 221 flows into second sieve bed 222 via equalization orifice 223. As a result, the removal of nitrogen from the second sieve bed 222, which is in the dump phase, is facilitated. It is further noted that the rate at which the pressure of first sieve bed 221 increases is a function of multiple factors, including, without limitation: the pump flow characteristics of pump 202; the volume of first sieve bed 221; the size of equalization orifice 223; and, once the pressure in first sieve bed 221 equals the pressure in product tank 249, the volume of product tank 249.

After the currently filling sieve bed, i.e., first sieve bed 221, is saturated with nitrogen or is approaching saturation, equalization phase 301 is performed, i.e., the equalization phase 301 that occurs between first dump/fill phase 302 and second dump/fill phase 303. Equalization phase 301 begins when first sieve bed fill valve 231 and second sieve bed fill valve 233 open, while first sieve bed dump valve 232 and second sieve bed dump valve 234 close. As a result, pressure in first sieve bed 221 and second sieve bed 222 equalizes via equalization orifice 223, so that the pressure in what was the filling sieve bed (i.e., first sieve bed 221) is used to quickly increase pressure in what was the non-filling sieve bed (i.e., second sieve bed 222). During this equalization step 301, first sieve bed 221 and second sieve bed 222 both receive air from pump 202 without any exhausting of gases.

Upon completion of equalization phase 301, second dump/fill phase 303 begins, in which first sieve bed 221 is exhausted to ambient via first sieve bed dump valve 232, and second sieve bed 222 is filled via second sieve bed fill valve 233. The above-described process then repeats and alternates between first sieve bed 221 and second sieve bed 222 to cyclically charge product tank 249 with an oxygen-enriched gas, such as oxygen-enriched product gas 132 in FIG. 1.

In sum, FIG. 3 depicts the pressure waveforms of first sieve bed 221, second sieve bed 222, and product tank 249 when the conventional oxygen concentrator supplies a constant flow of oxygen-enriched gas via the above-described PSA oxygen concentrator process. The saw tooth profile of product tank pressure 321 shows the increase of pressure of filling from one of first sieve bed 221 and second sieve bed 222, and the subsequent linear reduction in pressure during draining due to the constant flow delivery of the oxygen-enriched gas from product tank 249. The rate of decay (slope) 305 in product tank pressure 321 when not filling is a function of the volume of product tank 249 and the flow rate at which the oxygen-enriched gas is delivered from product tank 249. For example, when such a flow rate is reduced, the slope 305 becomes less negative.

It is noted that the increase in product tank pressure 321 continues until a dump/fill phase ends, and the time duration of each dump/fill phase is generally set as a predetermined cycle time. Alternatively, controller 250 is configured to adjust the min-to-max range of product tank pressure 321 during operation for a particular product flow rate (i.e., slope 305) by adjusting a control output in the conventional oxygen concentrator to modify operation of the conventional oxygen concentrator. For example, controller 250 may adjust the timing of one or more valves in the conventional oxygen concentrator, or may adjust an output of pump 202 in oxygen concentrator 130. Thus, the maximum product tank pressure 321 can be increased by controller 250, thereby increasing the quantity of oxygen-enriched product gas 132 that is stored in product tank 249.

According to embodiments of the invention, the output of oxygen concentrator 130, as shown in FIG. 1A, can be fluidly connected to respiratory ventilation device 120, which does not provide a constant flow of inhalation gas 123 to patient 101. Instead, respiratory ventilation device 120 provides inhalation gas 123 to patient 101 intermittently, typically in response to an inspiratory effort by patient 101. As a result, oxygen-enriched product gas 132 is delivered from product tank 249 of oxygen concentrator 130 in intermittent pulses, rather than at a constant flow rate. Consequently, the pressure waveforms of first sieve bed 221, second sieve bed 222, and product tank 249 of oxygen concentrator 130 behave differently than depicted in FIG. 3. Such behavior is illustrated in FIG. 4.

Figure 4:
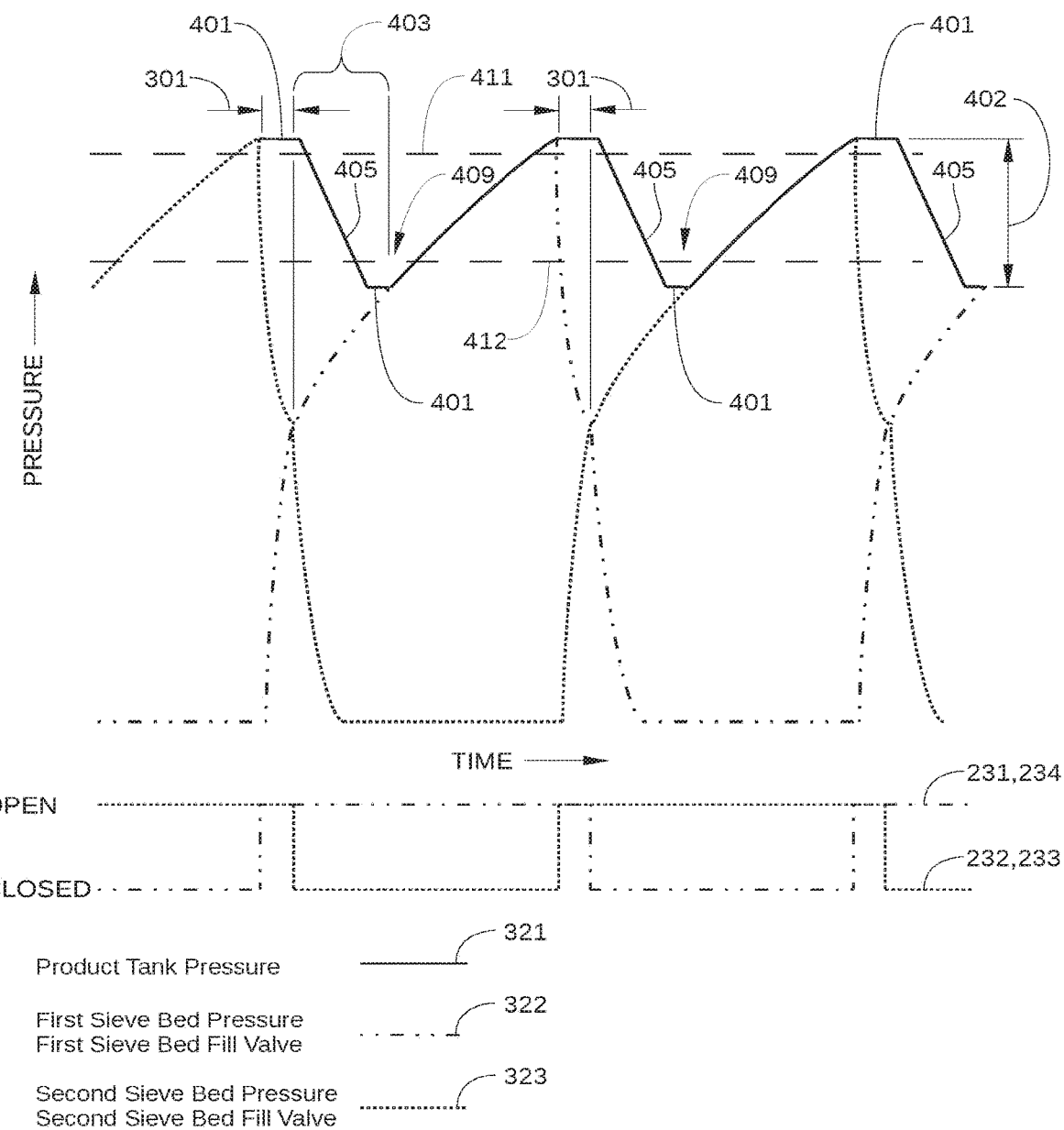
FIG. 4 is a graph illustrating pressure at various locations within a conventional oxygen concentrator as the conventional oxygen concentrator provides an intermittent volume of oxygen-enriched gas to a respiratory ventilation device.

FIG. 4 is a graph illustrating pressure at various locations within a conventional oxygen concentrator while the oxygen concentrator provides an intermittent volume of oxygen-enriched gas to respiratory ventilation device 120. The conventional oxygen concentrator may be substantially similar to oxygen concentrator 130, except without accumulator tank 247. The process by which such an oxygen concentrator provides oxygen-enriched product gas 132 may be substantially similar to by which oxygen concentrator 130 delivers a constant flow, and includes equalization phase 301, first dump/fill phase 302, and second dump/fill phase 303. However, as shown in FIG. 4, in a spontaneous delivery scenario, the pressure waveform behavior of product tank pressure 321 can be significantly different than in the constant flow delivery scenario illustrated in FIG. 3. In a spontaneous delivery scenario, respiratory ventilation device 120 spontaneously and intermittently delivers inhalation gas 123, which includes oxygen-enriched gas 132 from product tank 249 of oxygen concentrator 120. In such a spontaneous delivery scenario, the pressure waveform behavior of product tank 249 includes constant pressure intervals 401 and pressure drops 402.

Constant pressure intervals 401, i.e., the horizontal segments of product tank pressure 321, indicate that respiratory ventilation device 120 is not delivering inhalation gas 123 to patient 101 at a time that a sieve bed is not delivering oxygen-enriched gas to product tank 249. That is, the presence of a constant pressure interval 401 indicates that respiratory ventilation device 120 is not delivering inhalation gas 123 to patient 101 either during equilibrium phase 301 or during a portion 403 of a fill phase in which product tank pressure 321 is greater than either first sieve bed pressure 322 or second sieve bed pressure 323. By contrast, pressure decay slopes 405 result when respiratory ventilation device 120 spontaneously delivers inhalation gas 123 and a significant portion of the oxygen-enriched product gas 132 stored in product tank 249 exits product tank 249. Pressure decay slope 405 is a function of the flow rate of oxygen-enriched gas 132 from the oxygen concentrator to respiratory ventilation device 120 and the volume of product tank 249. Furthermore, the magnitude of pressure drop 402 (which occurs during a time that a sieve bed is not delivering oxygen-enriched gas to product tank 249) is a function of the quantity of oxygen-enriched gas delivered from the oxygen concentrator and the volume of product tank 249.

For clarity of description, in the embodiment of FIG. 4, the behavior of the pressure waveforms within the oxygen concentrator have been simplified. Specifically, the frequency of patient respiration is assumed to be essentially equal to that of the frequency of the dump/fill cycle of product tank 247. As a result, a single pressure decay slope 405 is shown for each dump/fill cycle of product tank 247. In practice, the phase and frequency of patient respiration is independent of the phase and frequency of the product tank dump/fill cycle. Consequently, patient inhalation can occur at a time that causes a pressure decay slope 405 to occur when product tank pressure 321 is already at a low pressure state 409, such as immediately before the most recently charged sieve bed has begun delivering oxygen-enriched product gas 132 to product tank 247. In such a scenario, the volume of oxygen-enriched product gas 132 delivered to patient 101 by respiratory ventilation device 120 can cause product tank pressure 321 to drop below the target supply pressure of pressure regulator 242. When the pressure in the portion of product gas supply stage 240 that is downstream of pressure regulator 242 falls below such a target delivery pressure, the flow rate of oxygen-enriched product gas 132 to respiratory ventilation device 120 generally drops below a target flow rate, and patient 101 receives less oxygen-enriched product gas 132 than expected.

According to various embodiments, accumulator tank 247 is employed in oxygen concentrator 130 to prevent the above-described scenario in which product tank depletion occurs. The presence of accumulator tank 247 in product gas supply stage 240 significantly modifies the pressure wave behavior of product tank pressure 321, as described below in conjunction with FIG. 5 and FIG. 6.

Figure 5:
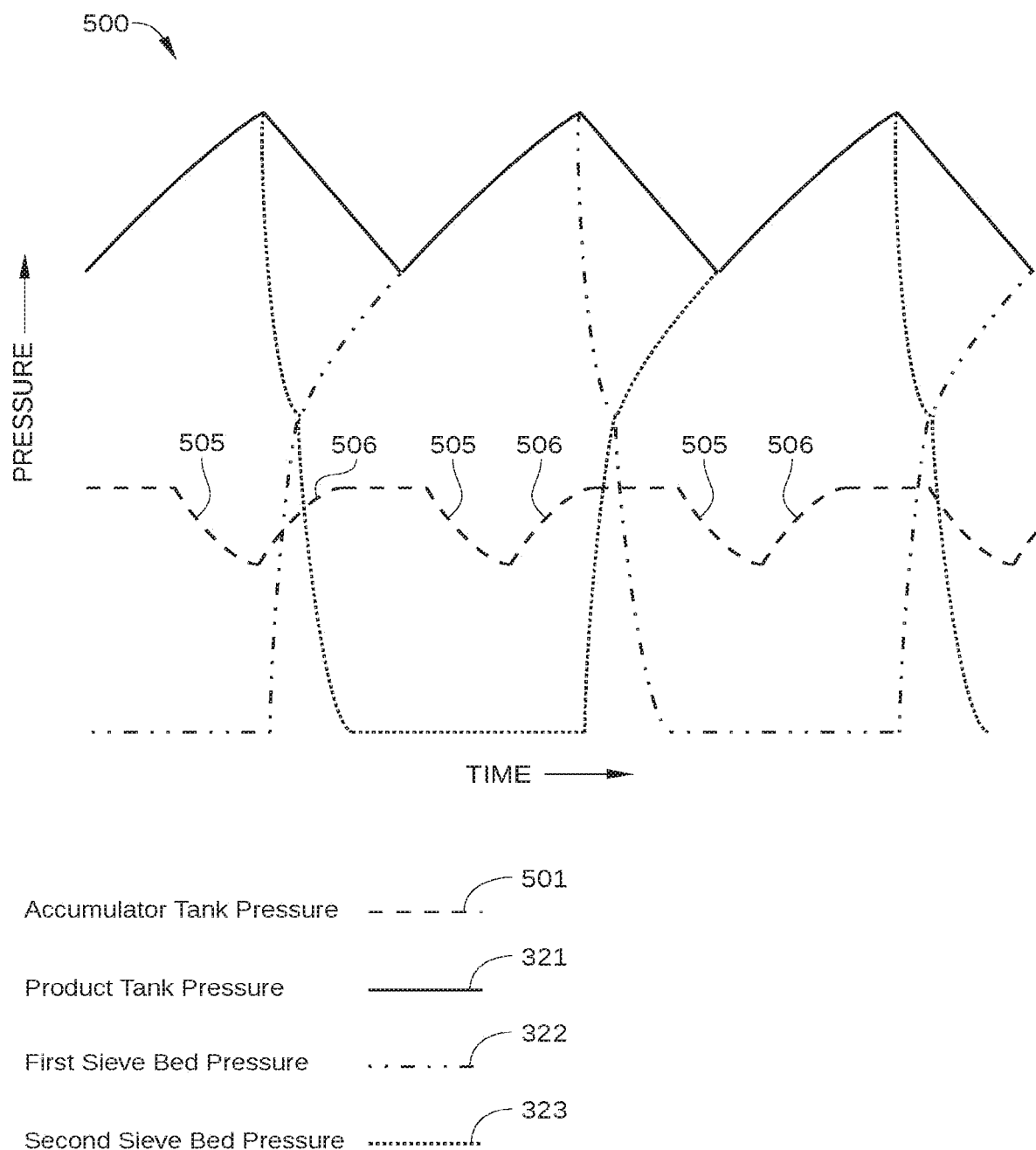
FIG. 5 is a graph illustrating pressure at various locations within the oxygen concentrator of FIG. 2 as the oxygen concentrator provides an intermittent volume of oxygen-enriched gas to a respiratory ventilation device, according to various embodiments of the invention.

FIG. 5 is a graph 500 illustrating pressure at various locations within oxygen concentrator 130 as oxygen concentrator 130 provides an intermittent volume of oxygen-enriched gas to respiratory ventilation device 120, according to various embodiments of the invention. Specifically, graph 500 shows the pressure waveforms of first sieve bed 221 (i.e., first sieve bed pressure 322), second sieve bed 222 (i.e., second sieve bed pressure 323), and product tank 249 (i.e., product tank pressure 321). In addition, graph 500 shows the pressure waveform of accumulator tank 247 as accumulator tank pressure 501. It is noted that the embodiment of accumulator tank pressure 501 illustrated in FIG. 5 is for a constant volume embodiment of accumulator tank 247, rather than a constant pressure embodiment of accumulator tank 247.

As shown, accumulator tank pressure 501 varies over time in response to a volume demand from respiratory ventilation device 120, i.e., when respiratory ventilation device 120 spontaneously delivers inhalation gas 123 to patient 101. During such delivery of inhalation gas 123 (which includes oxygen-enriched product gas 132 from oxygen concentrator 130), a portion of the oxygen-enriched product gas 132 stored in accumulator tank 247 exits accumulator tank 247, accumulator tank pressure 501 drops, and additional oxygen-enriched product gas 132 stored in product tank 249 flows into accumulator tank 247. Consequently, even though a significant volume of oxygen-enriched product gas 132 exits accumulator tank 247 during delivery of oxygen-enriched product gas 132 to respiratory ventilation device 120, accumulator tank pressure 501 only drops slightly, as indicated by pressure decay slopes 505. Further, because the volume demand from respiratory ventilation device 120 is satisfied with oxygen-enriched product gas 132 stored in accumulator tank 247, the only flow of oxygen-enriched product gas 132 from product tank 249 is at the constant flow rate determined by manual flow-control device 245. It is noted that the flow capacity of accumulator tank 247 is generally significantly higher than the rate of flow allowed by manual flow-control device 245.

Once delivery of inhalation gas 123 ceases, flow of oxygen-enriched product gas 132 out of accumulation tank 247 also ceases, while oxygen-enriched product gas 132 continues to flow into accumulator tank 247. Consequently, accumulator tank pressure 501 increases with a pressure rise slope 506 until another delivery of inhalation gas 123 occurs, or until accumulator tank pressure 501 reaches the target delivery pressure of pressure regulator 242. The slope of pressure rise slope 506 is a function of multiple factors, including the volume of accumulator tank 247, the setting of manual flow-control device 245, the quantity of oxygen-enriched product gas 132 just delivered to patient 101, and the target delivery pressure of setting of pressure regulator 242.

The slope of pressure decay slope 506 is a function of multiple factors, including the volume of accumulator tank 247, the flow rate at which the oxygen-enriched product gas 132 is delivered from accumulator tank 247 to respiratory ventilation device 120, and the rate at which oxygen-enriched product gas 132 flows into accumulator tank 247 from product tank 249. Thus, when accumulator tank 247 is sized appropriately, a low-volume, constant flow demand is placed on product tank 249 during delivery of oxygen-enriched product gas 132 to respiratory ventilation device 120. As a result, product tank pressure 321 shows similar behavior to that when oxygen concentrator 130 is coupled to ambient pressure delivery device 140, and is shown in FIG. 5. Specifically, in such an embodiment, product tank pressure 321 includes no or very brief constant pressure intervals or steep pressure drops, such as constant pressure intervals 401 and pressure drops 402 in FIG. 4. Instead, product tank pressure 321 shows the saw tooth profile associated with the pressure increase during filling from one of first sieve bed 221 and second sieve bed 222, and the subsequent linear reduction in product tank pressure during draining due to the constant flow delivery of the oxygen-enriched gas from product tank 249 to accumulator tank 247.

In some embodiments, accumulator tank 247 can be sized to store a quantity of oxygen-enriched product gas 132 that is approximately equal to or greater than a typical volume of oxygen-enriched product gas 132 that is expected to be delivered during a single patient respiratory effort. In such embodiments, accumulator tank pressure 501 may drop significantly, depending on the minimum inlet pressure of respiratory ventilation device 120. However, due to the presence of manual flow-control device 245 and pressure regulator 242 between accumulator tank 247 and product tank 249, the pressure swings experienced by accumulator tank pressure 501 are generally not reflected in product tank pressure 321.

In embodiments in which the preferred supply/inlet pressure of respiratory ventilation device 120 falls within a relatively narrow pressure range, accumulator tank 247 can be sized to prevent unwanted pressure swing in the portion of product gas supply stage 240 proximate output 131 of oxygen concentrator 130. In such embodiments, accumulator tank 247 can be sized to have a sufficient storage volume (when at a peak pressure) to store a quantity of oxygen-enriched product gas 132 that is at least about two times that of a typical volume of oxygen-enriched product gas 132 that is expected to be delivered during a single patient respiratory effort. In such embodiments, the peak pressure is typically equal to the target (i.e., downstream) pressure of pressure regulator 242. Thus, once accumulator tank 247 reaches the peak pressure, a single delivery of oxygen-enriched product gas 132 to patient 101 can be mostly or entirely satisfied by accumulator tank 247. As a result, the pressure in the portion of product gas supply stage 240 disposed between pressure regulator 242 and accumulator tank 247 will not drop significantly below the target delivery pressure of pressure regulator 242, and product tank 249 will not undergo a steep pressure decay.

Figure 6:
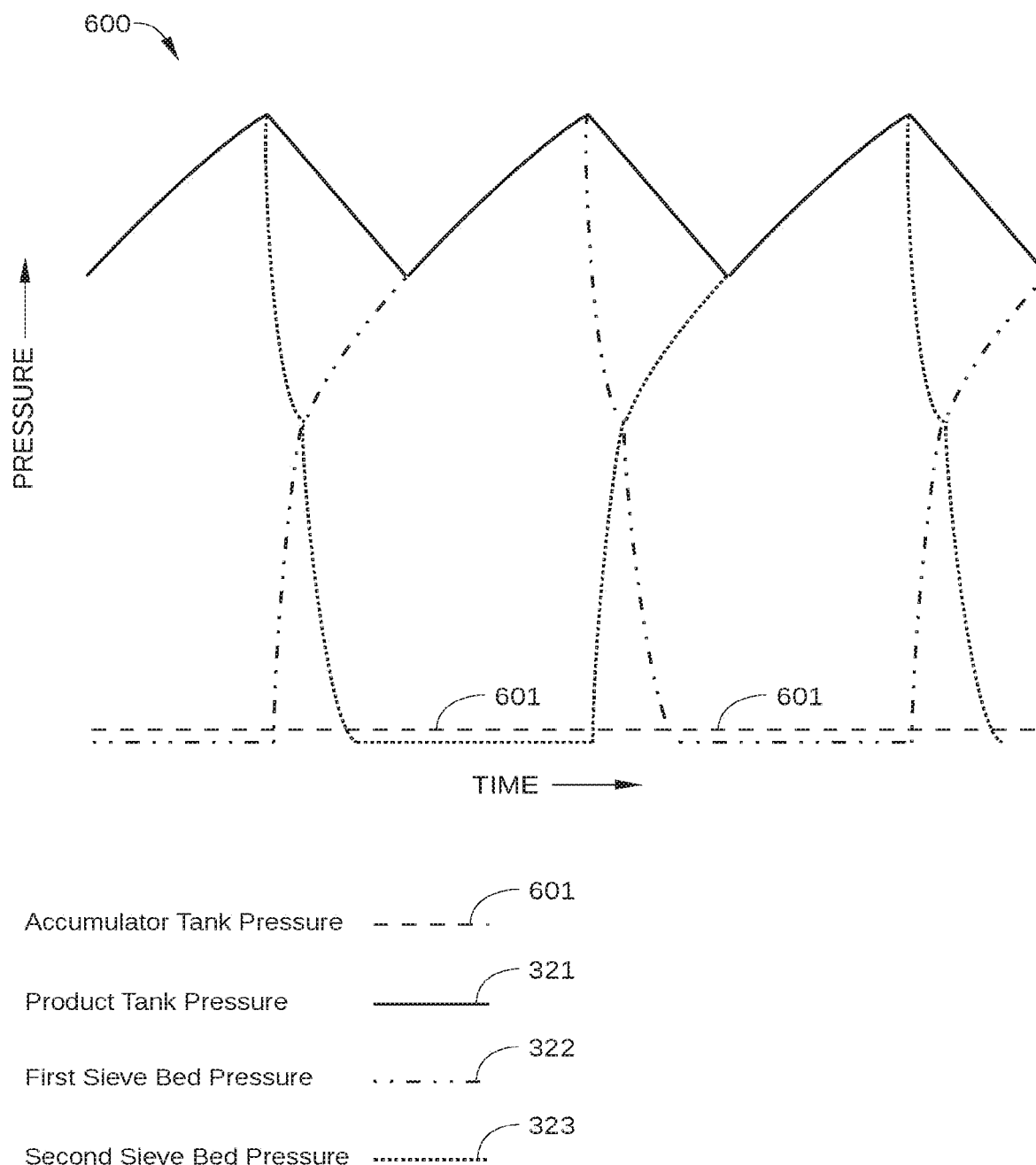
FIG. 6 is a graph illustrating pressure at various locations within the oxygen concentrator of FIG. 2 as oxygen concentrator provides a constant flow of oxygen-enriched gas to an ambient pressure delivery device, according to various embodiments of the invention.

FIG. 6 is a graph 600 illustrating pressure at various locations within oxygen concentrator 130 as oxygen concentrator 130 provides a constant flow of oxygen-enriched gas to an ambient pressure delivery device 140, according to various embodiments of the invention. Specifically, graph 600 shows the pressure waveforms of first sieve bed 221 (i.e., first sieve bed pressure 322), second sieve bed 222 (i.e., second sieve bed pressure 323), and product tank 249 (i.e., product tank pressure 321). In addition, graph 600 shows the pressure waveform of accumulator tank 247 as accumulator tank pressure 601. It is noted that the embodiment of accumulator tank pressure 601 illustrated in FIG. 6 is for a constant volume embodiment of accumulator tank 247, rather than a constant pressure embodiment of accumulator tank 247.

As shown, accumulator tank pressure 601 remains constant and only slightly above ambient pressure. Specifically, accumulator tank pressure 601 is a function of the flow rate as set by manual flow-control device 245 and the pressure drop characteristics of ambient pressure delivery device 140 and tubing associated therewith. Furthermore, it is noted that product tank pressure 321 includes no or very brief constant pressure intervals or steep pressure drops, such as constant pressure intervals 401 and pressure drops 402 in FIG. 4, and instead shows the saw tooth profile associated with the pressure increase during filling from one of first sieve bed 221 and second sieve bed 222, and the subsequent linear reduction during draining due to the constant flow delivery of the oxygen-enriched gas from product tank 249 to accumulator tank 24y and patient 101. Thus, as illustrated by FIGS. 5 and 6, oxygen concentrator 130 can operate effectively when providing oxygen-enriched product gas 132 to either ambient pressure delivery device 140 or respiratory ventilation device 120.

In sum, embodiments of the present invention provide an oxygen concentrator that is configured for use in conjunction with a mechanical ventilator and an ambient pressure delivery device. Specifically, an accumulator tank is disposed proximate the outlet of the oxygen concentrator, so that some or all of the product gas supplied to the mechanical ventilator during a period of volume demand is provided by the accumulator tank, rather than a product tank of the oxygen accumulator.

At least one advantage of the disclosed design is that pressure swing effects are reduced or avoided in the product tank when the oxygen concentrator is coupled to a mechanical ventilator. Thus, a more constant flow of product gas to the mechanical ventilator is provided relative to prior art designs.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

The invention has been described above with reference to specific embodiments. Persons of ordinary skill in the art, however, will understand that various modifications and changes may be made thereto without departing from the broader spirit and scope of the invention as set forth in the appended claims. For example, and without limitation, although many of the descriptions herein refer to devices, persons skilled in the art will appreciate that the systems and techniques described herein are applicable to other types of devices. The foregoing description and drawings are, accordingly, to be regarded in an illustrative rather than a restrictive sense.

What is claimed is:

1. An apparatus, comprising:
   at least one sieve bed configured to provide oxygen-enriched gas;
   a product tank arranged downstream of the at least one sieve bed and configured to receive the oxygen-enriched gas from the at least one sieve bed;
   an outlet port configured to be connected to a respiratory ventilation device;
   a product gas accumulator tank downstream of the product tank and at the outlet port;
   a tank pressure measurement device configured to measure pressure of the oxygen-enriched gas in the product tank;
   a flow measurement device arranged between the product tank and the product gas accumulator tank, the flow measurement device configured to measure flow of oxygen-enriched product gas;
   a pressure regulator arranged between the product tank and the product gas accumulator tank, the pressure regulator configured to regulate a pressure of the oxygen-enriched gas flowing from the product tank at a product tank pressure down to a target delivery pressure; and
   a controller configured to receive one or more pressure measurements from the tank pressure measurement device and receive one or more flow measurements from the flow measurement device, the controller further configured to control flow to the product gas accumulator tank;
   wherein the apparatus is configured such that, when the outlet port is connected to the respiratory ventilation device, the product gas accumulator tank stores a quantity of the oxygen-enriched gas received from the product tank between each of a plurality of patient inspiratory efforts and supplies the stored oxygen-enriched gas at a consistent flow rate to the outlet port during each of the plurality of patient inspiratory efforts.

2. The apparatus of claim 1, wherein the product tank is fluidly coupled to the at least one sieve bed via a check valve that allows flow from the at least one sieve bed to the product tank.

3. The apparatus of claim 1, further comprising a filter, wherein the product gas accumulator tank is disposed between the filter and the outlet port.

4. The apparatus of claim 1, further comprising an oxygen sensor that is arranged between the product tank and the product gas accumulator tank.

5. The apparatus of claim 1, wherein the product gas accumulator tank comprises either a constant volume pressure vessel or a variable volume pressure vessel.

6. The apparatus of claim 5, wherein the variable volume pressure vessel comprises a balloon accumulator or a movable piston.

7. The apparatus of claim 6, wherein the movable piston, during operation, maintains a substantially constant pressure in the variable volume pressure vessel.

8. A system, comprising:
   a respiratory ventilation device; and
   an oxygen concentrator that includes:
      at least one sieve bed configured to provide oxygen-enriched gas;
      a product tank arranged downstream of the at least one sieve bed and configured to receive the oxygen-enriched gas from the at least one sieve bed;
      an outlet port configured to be connected to the respiratory ventilation device;
      a product gas accumulator tank arranged downstream of the product tank and at the outlet port;
      a tank pressure measurement device configured to measure pressure of the oxygen-enriched gas in the product tank;
      a flow measurement device arranged between the product tank and the product gas accumulator tank, the flow measurement device configured to measure flow of oxygen-enriched product gas;
      a pressure regulator arranged between the product tank and the product gas accumulator tank, the pressure regulator configured to regulate a pressure of the oxygen-enriched gas flowing from the product tank at a product tank pressure down to a target delivery pressure; and
      a controller configured to receive one or more pressure measurements from the tank pressure measurement device and one or more flow measurements from the flow measurement device;
      wherein the oxygen concentrator is configured such that, when the outlet port is connected to the respiratory ventilation device, the product gas accumulator tank stores a quantity of oxygen-enriched gas received from the product tank between each of a plurality of patient inspiratory efforts and supplies the stored oxygen-enriched gas at a consistent flow rate to the outlet port during each of the plurality of patient inspiratory efforts.

9. The system of claim 8, wherein the product tank is fluidly coupled to the at least one sieve bed via a check valve that allows flow from the at least one sieve bed to the product tank.

10. The system of claim 8, the oxygen concentrator further comprising a filter, wherein the product gas accumulator tank is disposed between the filter and the outlet port of the oxygen concentrator.

11. The system of claim 8, further comprising an oxygen sensor that is arranged between the product tank and the product gas accumulator tank.

12. The system of claim 8, wherein the product gas accumulator tank comprises either a constant volume pressure vessel or a variable volume pressure vessel.

13. The system of claim 12, wherein the variable volume pressure vessel comprises a balloon accumulator or a movable piston.

14. The system of claim 13, wherein the movable piston, during operation, maintains a substantially constant pressure in the variable volume pressure vessel.

* * * * *